(12) United States Patent
Tian et al.

(10) Patent No.: US 9,186,348 B2
(45) Date of Patent: Nov. 17, 2015

(54) ORAL COMPOSITIONS FOR SKIN BENEFITS

(75) Inventors: Minmin Tian, Naperville, IL (US); Michael J. Greenberg, Northbrook, IL (US); Darci C. Chidichimo, Crown Point, IN (US)

(73) Assignee: WM. WRIGLEY JR. COMPANY, Chicago, IL (US)

( * ) Notice: Subject to any disclaimer, the term of this patent is extended or adjusted under 35 U.S.C. 154(b) by 0 days.

(21) Appl. No.: 13/265,012

(22) PCT Filed: Apr. 28, 2010

(86) PCT No.: PCT/US2010/032728
§ 371 (c)(1),
(2), (4) Date: Feb. 29, 2012

(87) PCT Pub. No.: WO2010/126982
PCT Pub. Date: Nov. 4, 2010

(65) Prior Publication Data
US 2012/0171273 A1      Jul. 5, 2012

Related U.S. Application Data

(60) Provisional application No. 61/173,263, filed on Apr. 28, 2009.

(51) Int. Cl.
*A61K 9/68*     (2006.01)
*A01N 43/16*    (2006.01)
*A61K 31/355*   (2006.01)
*A61K 9/00*     (2006.01)
*A61K 31/192*   (2006.01)
*A61K 31/375*   (2006.01)
*A61K 36/82*    (2006.01)
*A61K 45/06*    (2006.01)

(52) U.S. Cl.
CPC ............. *A61K 31/355* (2013.01); *A61K 9/0056* (2013.01); *A61K 9/0058* (2013.01); *A61K 31/192* (2013.01); *A61K 31/375* (2013.01); *A61K 36/82* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,107,281 A | 8/2000 | Jones et al. | |
| 6,124,268 A | 9/2000 | Ghosal | |
| 6,299,925 B1 | 10/2001 | Xiong et al. | |
| 6,814,958 B1 | 11/2004 | Sekimoto | |
| 6,900,240 B2 | 5/2005 | Empie et al. | |
| 2007/0292560 A1* | 12/2007 | Quan et al. | 426/3 |
| 2009/0117252 A1* | 5/2009 | Satake et al. | 426/597 |

FOREIGN PATENT DOCUMENTS

| | | |
|---|---|---|
| EP | 2022346 | 2/2009 |
| GB | 2385768 | 9/2003 |
| WO | 9318661 | 9/1993 |
| WO | 0048551 | 8/2000 |
| WO | 0100038 | 1/2001 |
| WO | 2006121985 | 11/2006 |
| WO | WO 2007132562 A1 * | 11/2007 |
| WO | WO 2008045579 A1 * | 4/2008 |

OTHER PUBLICATIONS

Halliday, Jess; "Taiyo launches high EGCg green tea extract" (online); Jun. 22, 2005, XP002586515; NUTRA ingredients—usa; URL:http://www.nutraingredients-usa.com/content/view/print/30805>.

Burke, K.E.; "Photodamage of the skin: protection and reversal with topical antioxidants."; Journal of Cosmetic Dermatology; Jul. 2004 LNKD-PUBMED: 17134430, vol. 3, No. 3, Jul. 2004; pp. 149-155; XP002586516; ISSN: 1473-2165, p. 152.

Dai, F. et al; "Antioxidant synergism of green tea polyphenols with alpha-tocopherol and I-ascorbic acid in SDS micelles"; Biochimie, Masson, Paris, FR LNKD-DOI: 10.1016/J.Biochi.2008.05.007, vol. 90, No. 10; Oct. 1, 2008; pp. 1499-1505, XP025405376; ISSN: 0300-9084.

Katiyar, S.K. et al: "Green tea polyphenolic antioxidants and skin photoprotection (Review)", International Journal of Oncology, Demetrios A. Spandidos Ed. & Pub, GR, vol. 18, No. 6; Jun. 1, 2001; pp. 1307-1313; XP009119640; ISSN: 1019-6439; p. 1309-1311.

Katiyar, Santosh K et al: "Green tea polyphenol (–)-epigallocatechin-3-gallate treatment to mouse skin prevents UVB-induced infiltration of leukocytes, depletion of antigen-presenting cells, and oxidative stress"; Journal of Leukocyte Biology, vol. 69, No. 5; May 2001, pp. 719-726; XP002586517; ISSN: 0741-5400; p. 721-725.

International Search Report, PCT Application PCT/US2010/032728, mail date Jan. 7, 2010.

* cited by examiner

*Primary Examiner* — Dennis J Parad
(74) *Attorney, Agent, or Firm* — Rebecca A. Aumann

(57) ABSTRACT

Oral compositions containing a combination of antioxidants consisting of a water soluble vitamin, a water insoluble vitamin, a tea extract and gallic acid are used to maintain a beneficial amount of such antioxidants in a consumers bloodstream for maintenance and protection of healthy skin. The unique combination of ingredients provides a decrease in oxidative stress when exposed to UVB radiation, thereby promoting healthy skin.

4 Claims, No Drawings

US 9,186,348 B2

ORAL COMPOSITIONS FOR SKIN BENEFITS

BACKGROUND OF THE INVENTION

This invention relates to oral compositions useful to maintain healthy skin and more particularly, compositions containing a unique blend of antioxidants to decrease oxidative stress in a consumer thereby providing and maintaining healthy skin.

The solar ultraviolet light (UV) that reaches the earth's surface is divided into two components, UVB (280-320 nm) and UVA (320-380 nm). The UVB component, which is directly absorbed by cellular macromolecules including DNA and protein, may cause DNA photodamage and mutagenesis. In humans, both acute and chronic exposures to sunlight are associated with various physiological and pathological states. The acute response leads to immediate effects such as erythema, sunburn, pigmentation, hyperplasia, immunosuppression and vitamin D synthesis, and the chronic response leads to delayed effects such as cataract, skin ageing and cancer. Skin ageing is characterized clinically by coarseness, wrinkles, mottled pigmentation, sallowness, laxity, premalignant, and ultimately malignant neoplasms. Skin ageing commonly occurs in skin that is habitually exposed to sunlight, such as the face, ears, bald areas of the scalp, neck, forearms, and hands.

It is known that most of these effects are wavelength dependent and usually occur as a result of cumulative solar UV dose, thereby causing oxidative stress and inducement of apoptosis. In photodermatological studies, special attention has been given to sunburn keratinocytes. The sunburn cells were originally discovered in the epidermis of mammalian cells exposed to UVB radiation and later regarded as an example of apoptosis. Dysregulation of the apoptotic mechanism in skin can lead to erythema multiforme, lichen planus, papillomas and skin cancer.

Sunscreens are commonly used to prevent skin ageing, and the formation of apoptotic sunburn keratinocytes that are exposed to sunlight. Sunscreens are topical preparations that contain ingredients that absorb, reflect, and/or scatter UV light. Because such preparations are often visible or occlusive, and many people consider these formulations cosmetically unacceptable. While some sunscreens may be more acceptable cosmetically, they are still relatively short-lived and susceptible to being removed by washing or perspiration. Topical applications can be messy, leave skin surface residue, emit unpleasant odors and are not convenient to apply.

Generally, vitamins, tea extracts and gallic acid have been shown to possess strong anti-oxidative characteristics in both dietary supplements and topical applications. Although these antioxidants have been used widely in a variety of product forms, there are few studies on the oral intake of combinations of antioxidants for protection and maintenance of healthy skin.

Accordingly, it would be desirable to provide a consumer friendly delivery vehicle which overcomes the deficiencies of topical therapies (over the counter (OTC) and prescription) for maintenance and protection of healthy skin.

SUMMARY OF THE INVENTION

Oral compositions containing a combination of antioxidants consisting of a water soluble vitamin, a water insoluble vitamin, a tea extract and gallic acid are used to maintain a beneficial amount of such antioxidants in a consumer's bloodstream for maintenance and protection of healthy skin. The unique combination of ingredients provides a decrease in oxidative stress when exposed to UVB radiation, thereby promoting healthy skin.

DESCRIPTION OF THE INVENTION

The present invention is directed to inhibiting (i.e., reducing or preventing) apoptosis in cells caused by exposure to UVB. Treatment according to this invention is preferably practiced via oral administration, affecting various areas of human skin such as that of the head, neck, hands, and arms that are typically exposed to sunlight from habitual, everyday living. As used herein, "skin" is the outer covering of the body, also known as the epidermis. It is the largest organ of the integumentary system made up of multiple layers of epithelial tissues, and guards the underlying muscles, bones, ligaments and internal organs.

Apoptosis is a form of programmed cell death in multicellular organisms. It is one of the main types of programmed cell death (PCD) and involves a series of biochemical events leading to a characteristic cell morphology and death, in more specific terms, a series of biochemical events that lead to a variety of morphological changes, including blebbing (formation of blebs, irregular bulge in the plasma membrane of cells caused by localized decoupling of the cytoskeleton from the plasma membranes), changes to the cell membrane such as loss of membrane asymmetry and attachment, cell shrinkage, nuclear fragmentation, chromatin condensation, and chromosomal DNA fragmentation (1-4). The induction of apoptosis in cells appears to be related to numerous factors. Some are related to the loss of survival factors or deregulation of survival pathways, i.e. cells that are exposed to environmental oxidants induce several antioxidant protective mechanisms.

It is known that apoptosis can be induced by oxidative stress. Oxidative stress is caused by an imbalance between the production of reactive oxygen and a biological system's ability to readily detoxify the reactive intermediates or easily repair the resulting damage. All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids, and DNA. If the combined constitutive and induced protective pathways do not suffice to counteract the action of oxidative components, cells will either undergo apoptosis or accumulate genetic changes that may then be involved in the process of carcinogenesis.

The formation of apoptotic sunburn keratinocytes was evidence that UVB triggers apoptosis in mammalian cells. Mechanistic studies in this field revealed evidence for the requirement of DNA damage and the induction of the p53 gene for UVB-induced sunburn cell formation (or apoptotic cells). Antioxidants and thiol reductants such as N-acetylcysteine, and overexpression of thioredoxin commonly delay or inhibit apoptosis. Alternatively, drugs such as buthionine sulfoximine deplete intracellular glutathione (GSH), thereby rendering cells more susceptible to apoptosis induced by oxidative stress.

Sunscreens are topical preparations that contain ingredients that absorb, reflect, and/or scatter UV light. Other topical forms include solutions, lotions, shake lotions, creams, ointments and gels. Sunscreens are commonly used to prevent skin ageing, and the formation of apoptotic sunburn keratinocytes that are exposed to sunlight. Some sunscreens are based on opaque particulate materials, among them zinc oxide, titanium oxide, clays, and ferric chloride. Because such preparations are visible and occlusive, many people consider these opaque formulations cosmetically unacceptable. Other sunscreens contain chemicals such a p-aminobenzoic acid (PABA), oxybenzone, dioxybenzone, ethylhexylmethoxy cinnamate, octocrylene, octyl methoxycinnamate, and butylmethoxydibenzoylmethane that are transparent or translucent on the skin. While these types of sunscreens may be more acceptable cosmetically, they are still relatively short-lived and susceptible to being removed by washing or perspiration.

Antioxidants play a crucial defensive role in UVB-induced apoptosis. Oxidative stress activates apoptosis, and antioxidants protect against apoptosis in vitro; thus, a central role of dietary antioxidants may be to protect against apoptosis. However, little in vivo data is available to directly link diet with altered apoptosis as an underlying determinant of disease. Moreover, there are possible antagonistic effects of when different antioxidant components are combined.

Compositions of this invention provide efficacious levels of antioxidants in the bloodstream of a consumer for skin health, maintenance, and protection thereby yielding anti-aging and anti-wrinkling effects without requiring a prescription, and without the need of a topical application. The term "efficacious" means producing or capable of producing a desired effect. When used in respect to an "effective amount" the term refers to the level, amount, serving, or percent that is required to produce or is capable of producing a desired effect. Further, the antioxidants of the present invention have been found to work without antagonism in decreasing oxidative stress as measured by the development of apoptotic cells following exposure to UVB radiation.

Non-limiting examples of the present invention can take any physical form suitable for application to an oral surface and provides either a cosmetic prophylactic or therapeutic benefit within or derived from the oral cavity. In various embodiments, the oral composition can be a dentifrice such as a powder, spray or foam; an edible film or a bioadhesive film; a confectionary composition including but not limiting to breath mints, liquid filled beads, low boiled candy, chewing gum, chewy candy, hard boiled candy, coated candy, lozenges, syrups, pressed mints, chocolates and the like. In certain embodiments, the consuming, masticating or adhering of the oral composition is repeated at regular intervals.

The oral compositions of this invention eliminates a need for having fluids available for swallowing large pills, and is gentler on the stomach. As used herein, "chewable compositions" refers to a variety of forms which are chewed in the mouth after oral administration, or slowly dissolve after oral administration. This is particular helpful for those having difficulty in swallowing and for those having gastrointestinal difficulties.

All percentages used herein are by weight of the total composition and all measurements made are at 25° C., unless otherwise designated.

The oral compositions of the present invention may employ a variety of release mechanisms of the antioxidants, which include delayed, immediate, timed, controlled and variable, alone or in combination using known procedures in the art. In an aspect of the invention, the oral composition may utilize the process of encapsulation as a release mechanism for the antioxidants. Some examples of encapsulation procedures include but are not limited to spray drying, fluid-bed coating, spray chilling, coacervation, agglomeration, fixation, absorption, and entrapment alone or in any combination yielding full or partial encapsulation. The antioxidants may be coated in a two-step process or multiple step process. The materials may be coated with any of the ingredients as described herein to obtain a coated product yielding improved crunch, sensory properties and/or stability.

The antioxidants useful in this invention include a water soluble vitamin, a water insoluble vitamin, a tea extract, and gallic acid and its derivatives thereof. As used herein, "extract" includes obtaining from a substance by chemical or mechanical action, as by pressure, distillation, or evaporation. For example, extracts may be obtained from any part of including the leaf, stem, bark, pulp, seed, flesh, juice, root and mixtures thereof. It is preferred that the extract is obtained from the leaf, pulp and seed, more preferably from the leaf or seed The extract may be derived from a natural, artificial source or organic source and combinations thereof. As used herein, "artificial" is something which is not natural. It refers to a product of human endeavor; a more English but gendered synonym is man-made.

A water soluble vitamin useful in this invention includes vitamin C.

For example, the water-soluble vitamin may be present in an oral composition at a concentration of from about 0.001% to about 20% by weight, from about 0.01% to about 10% by weight, or from about 0.1% to about 10% by weight. Or alternatively, the oral composition contains at least 0.3 mg to about 50 mg per serving, 50 mg to about 100 mg per serving or 100 mg to about 200 mg per serving.

The oral composition preferably contains a water soluble vitamin such as vitamin C in the range of about 100 mg to about 1000 mg, 400 mg to about 800 mg, or at least 600 mg of vitamin C or more per day to a consumer.

Vitamin C as described herein refers to any derivative, compound, or combination of compounds having vitamin C activity. Except where the context demands otherwise, the term "vitamin C" is used generically herein to encompass ascorbic acid, any of its salts, any of its derivatives from natural or artificial sources, including any enantiomer or racemate thereof, and any mixture of such compounds having vitamin C activity.

Non-limiting examples of vitamin C derivatives include calcium ascorbate, magnesium ascorbate, zinc ascorbate, potassium ascorbate, sodium ascorbate, dehydroascorbic acid, L-ascorbic acid 2-0-sulfate, L-ascorbic acid 2-0-phosphate, L-ascorbic acid 3-0-phosphate, L-ascorbic acid 6-hexadecanoate, L-ascorbic acid monostearate, L-ascorbic acid dipalmitate, L-threonic acid, L-xylonic acid, L-lyxonic acid and combinations thereof.

A water insoluble vitamin useful in this invention includes vitamin E.

In an aspect of the invention, vitamin E as described herein encompasses vitamin E acetate, natural and artificial tocopherols, alpha-tocopherol, beta-tocopherol, gamma-tocopherol, delta-tocopherol, combinations or derivatives thereof having vitamin E activity.

In another aspect, the water soluble may include alone or in combination, Thiamine (vitamin $B_1$), Riboflavin (vitamin $B_2$), Pyridoxine (Pyridoxal, vitamin $B_6$), Nicotinamide (Niacin), Pantothenic Acid, Biotin, Folic Acid, and Cyanocobalamin (vitamin $B_{12}$).

The water insoluble vitamin may be present in an oral composition at a concentration of from about 0.001% to about 10% by weight, from about 0.01% to about 5% by weight, or from about 0.1% to about 4% by weight. Or alternatively, the oral composition contains at least 1 mg to about 100 mg per serving, 10 mg to about 90 mg per serving or 30 mg to about 70 mg per serving of water insoluble vitamin.

The oral composition contains a water insoluble vitamin such a vitamin E in the range of about 10.0 mg to 100 mg, 100 mg to about 200 mg, or at least 200 mg of vitamin E or more per day to a consumer.

The extract of tea most useful in this invention is green tea. Green tea is a type of tea made solely with the leaves of *Camellia sinensis*, and has undergone minimal oxidation during processing. White tea, green tea, oolong, pu-erh tea and black tea are all harvested from this species, but are processed differently to attain different levels of oxidation. Green tea originates from China and has become associated with many cultures in Asia from Japan to the Middle East. Recently, it has become more widespread in the West, where black tea is traditionally consumed. Many varieties of green tea have been created in countries where it is grown. These varieties can differ substantially due to variable growing conditions, processing and harvesting time.

For example, the green tea extract may be present in an oral composition at a concentration of from about 0.001% to about 20% by weight, from about 0.01% to about 10% by weight, or from about 0.1% to about 10% by weight.

Preferably, the oral composition per serving (svg) comprises at least 2.0 mg/svg of green tea extract, at least 3.0 mg/svg of green tea extract, at least 4.0 mg/svg of green tea extract or at least 5.0 mg/svg of green tea extract. Still more preferably, the oral composition comprises at least 2.0 mg/svg of green tea extract having a total catechin content of at least 70%.

In another aspect, the green tea extract employed preferably comprises at least 5% by weight epigallocatechin gallate (EGCG), at least 15% by weight EGCG, at least 30% by weight EGCG, and at least 50% by weight EGCG.

In yet another example, the oral composition is consumed four times a day to deliver at least per 30 mg of EGCG per day to a consumer for efficacious results.

Chemical structures of the principle green tea catechins.

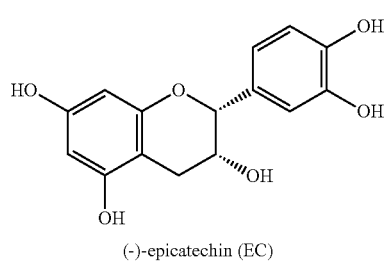

(-)-epicatechin (EC)

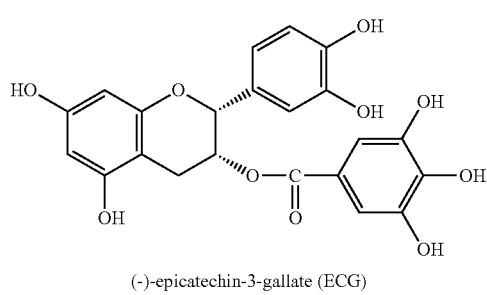

(-)-epicatechin-3-gallate (ECG)

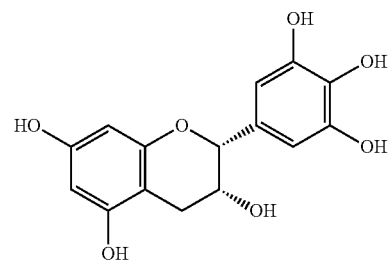

(-)-epigallocatechin (EGC)

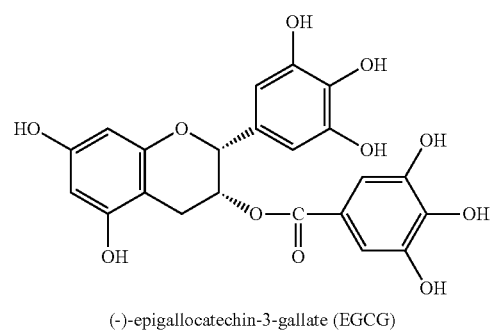

(-)-epigallocatechin-3-gallate (EGCG)

Table 1 summarizes the range of individual catechin contents in fresh tea leaf Green tea contains moderate amounts of caffeine, with caffeine contents up to 7%.

TABLE 1

Range of catechin contents (% dry wt) in fresh tea leaf.

| | | | |
|---|---|---|---|
| (−)-Epicatechin | 1-3% | (−)-Epigallocatechin | 3-6% |
| (−)-Epicatechin gallate | 3-6% | (−)-Epigallocatechin gallate | 7-13% |

For example, Sunphenon® 90M is a green tea catechin enriched extract prepared from the leaf of green tea (*Camellia sinensis*). The product specifications indicate that this product contains at least 75% total catechins, and at least 45% EGCG. Thus, this product may provide more catechin and more EGCG than from fresh tea leaf.

TABLE 2

Catechin contents in Sunphenon ® 90M determined by the HPLC analysis.

| | | | |
|---|---|---|---|
| (−)-Epicatechin | 4.9% | (−)-Epigallocatechin | 5.2% |
| (−)-Epicatechin gallate | 13.7% | (−)-Epigallocatechin gallate | 57.2% |

Gallic acid (GA), a food component that is especially abundant in tea, is an antimutagenic, anticarcinogenic and anti-inflammatory agent. Gallic acid (GA) is an endogenous product found in plants, and in free or bound forms, it is found in large amounts in tea leaves, from which it is usually extracted in hot water infusions. Gallic acid is an organic acid, also known as 3,4,5-trihydroxybenzoic acid, found in gallnuts, sumac, witch hazel, tea leaves, oak bark, and other plants. The chemical formula is $C_6H_2(OH)_3CO_2H$. Gallic acid is found both free and as part of tannins. Salts and esters of gallic acid are termed gallates.

Chemical structures of a) gallic acid; b) anion of gallic acid

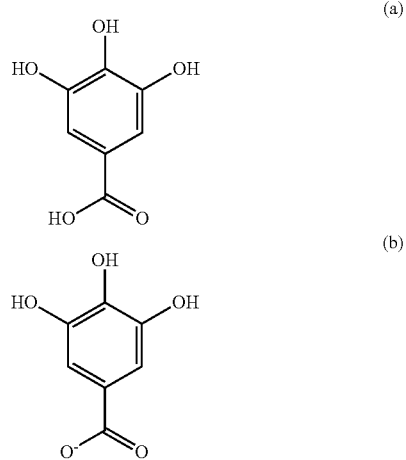

For example, the gallic acid may be present in an oral composition at a concentration of from about 0.001% to about 5% by weight, from about 0.01% to about 5% by weight, or from about 0.1% to about 2% by weight.

Preferably, the oral composition per serving (svg) preferably comprises at least 0.1 mg/svg of gallic acid, at least 1.0 mg/svg of gallic acid, at least 2.0 mg/svg of gallic acid or at least 4.0 mg/svg of gallic acid.

In yet another example, the oral composition is consumed four times a day to deliver at least 10.0 mg of gallic acid per day to a consumer for efficacious results.

The following examples are illustrative of preferred embodiments of the invention and are not to be construed as limiting the invention thereto. All percentages are based on the percent by weight of the composition unless otherwise indicated and all totals equal 100% by weight.

I. Oral Compositions

The term "oral composition" as used herein includes dentifrices such as a powders, sprays or foams; edible or a bioadhesive films; confectionary compositions including but not limiting to breath mints, liquid filled beads, low boiled candy, chewing gum, chewy candy, hard boiled candy, coated candy, lozenges, syrups, pressed mints, chocolates and the like. Ideally, the oral composition of the present invention is capable if being retained in the mouth for a period of time greater than 30 seconds to allow for complete release and absorption of the antioxidants by the oral mucosa and/or buccal tissues.

In a preferred embodiment, the oral composition is a chewing gum composition which is suitable for chewing and which comprises 2% or greater, by weight of the composition, of elastomer. In general, chewing gum compositions are chewed or masticated by consumers, the process by which food is mashed and crushed by teeth. Such chewing gum compositions can take a variety of shapes and forms, for example, a pellet, a gumball, a square, a stick, etc., and may be coated by a variety of materials including but not limiting to sugars, polyols, chocolates, syrups, films, etc., alone or in any combination.

The chewing gum of the present invention is preferably a sugarless chewing gum containing the antioxidant compounds. Chewing gum formulations typically contain, in addition to, a chewing gum base, one or more plasticizing agents, at least one sweetening agent and at least one flavoring agent.

Gum base materials suitable for use in the practice of this invention are well known in the art and include natural or artificial gum bases or mixtures thereof. Representative natural gums or elastomers include chicle, natural rubber, jelutong, balata, guttapercha, lechi caspi, sorva, guttakay, crown gum, perillo, or mixtures thereof. Representative artificial gums or elastomers include butadiene-styrene copolymers, polyisobutylene and isobutylene-isoprene copolymers. The gum base is incorporated in the chewing gum product at a concentration of about 10 to about 40% and preferably about 20 to about 35%.

Plasticizing/softening agents commonly used in chewing gum compositions are suitable for use in this invention, including gelatin, waxes and mixtures thereof in amounts of about 0.1 to about 5%. The sweetening agent ingredient used in the practice of this invention may be selected from a wide range of materials, and include the same artificial and polyol sweeteners used for the preparation of tablets, beads and lozenges. Polyol sweeteners such as sorbitol and maltitol are present in the chewing gum composition of the present invention in amounts of about 40 to about 80% and preferably about 50 to about 75%. The artificial sweetener is present in the chewing gum composition of the present invention in amounts of about 0.1 to about 2% and preferably about 0.3 to about 1%.

The orally acceptable vehicle or carrier in a lozenge bead or tablet is a non-cariogenic, solid water-soluble polyhydric alcohol (polyol) such as mannitol, xylitol, sorbitol, maltitol, hydrogenated starch hydrolysate, hydrogenated glucose, hydrogenated disaccharides or hydrogenated polysaccharides, in an amount of about 85 to about 95% of the total composition. Emulsifiers such as glycerin, and tableting lubricants, in minor amounts of about 0.1 to 5%, may be incorporated into the tablet, bead or lozenge formulation to facilitate the preparation of the tablet beads and lozenges. Suitable lubricants include vegetable oils such as coconut oil, magnesium stearate, aluminum stearate, talc, starch and CARBOWAX. Suitable noncariogenic gums include kappa carrageenan, carboxymethyl cellulose, hydroxyethyl cellulose and the like.

The lozenge, bead or tablet may optionally be coated with a coating material such as waxes, shellac, carboxymethyl cellulose, polyethylene/malic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet, bead and lozenge compositions of this embodiment affords a relatively longer time period of contact of the teeth in the oral cavity with the antioxidant ingredients of the present invention.

Bioadhesive films, syrups, sprays, microspheres, tablets, or films may also be employed. The bioadhesive polymers of this invention may be cross-linked by cross-linking agents as known in the art. Other suitable polymers include but are not limited to polyacrylic polymers such as, carhomer and carhomer derivatives; cellulose derivatives such as hydroxypropylmethylcellulose (HPMC), hydroxyethylcellulose (HEC), hydroxypropylcellulose (HPC) and sodium carboxymethylcellulose (NaCMC); natural polymers such as gelatin, sodium alginate, pectin; more generally, any physiologically acceptable polymer showing bioadhesive characteristics may be used successfully to coat controlled release units.

Preferably, the chewable composition also includes a trigeminal stimulant to provide hot, cold, tingling or irritating effects in the oral cavity of a consumer thereby increasing uptake of the antioxidant compounds to provide body surface benefits.

In a preferred embodiment, the oral composition comprises a trigeminal stimulant including but not limited to menthol and other cooling compounds such as WS-23 and other cooling carboxamide compounds, camphor, allyl isothiocyanate, capsaicin, diallyl sulfide alone or in combination.

The following examples are illustrative of preferred embodiments of the invention and are not to be construed as limiting the invention thereto. All percentages are based on the percent by weight of the composition unless otherwise indicated and all totals equal 100% by weight.

Example 1

Chewing gum formulations (designated "Compositions A, B, & C") were prepared containing the antioxidants for skin health.

| Ingredients | A Weight % | B Weight % | C Weight % |
|---|---|---|---|
| Gum Base | 31.00 | 30.45 | 31.00 |
| Sorbitol | 44.00 | — | 40.00 |
| Erythritol | — | 49.00 | — |
| Mannitol | — | — | 9.00 |
| Talc | 5.00 | — | — |
| Lycasin/Glycerin | 5.00 | 5.00 | 5.00 |
| Lecithin | 0.30 | 1.00 | 0.50 |
| High Intensity Sweetener | 1.00 | 1.00 | 1.00 |
| Flavor | 0.40 | 0.60 | 0.50 |
| Vitamin C | 6.70 | — | 2.80 |
| Sodium Ascorbate | — | 3.00 | — |
| Green Tea Extract Sunphenon ® 90M | — | 1.00 | 0.90 |
| Green Tea Extract (containing at least 40.0% EGCG) | 1.10 | — | 0.70 |
| Gallic Acid | 0.16 | 0.16 | 0.16 |
| Vitamin E[3] (tocopherol acetate) | 2.67 | 2.67 | 2.67 |

Example 2

Example 2 demonstrates antioxidant loading in chewing gum compositions of the present invention for repeat administration.

| | HPLC analysis of antioxidant loading and relative standard deviation | | | |
|---|---|---|---|---|
| Active Compound | Formula Input | Analytical Result | Relative Standard Deviation (RSD %) | N |
| Vitamin E[3] (Tocopherol Acetate)* | 40.5 mg | 31.04 mg/piece | 5.8% | 6 |
| Vitamin C | 100 mg/piece | 89.13 mg/piece | 2.1% | 6 |
| Gallic Acid | 2.5 mg/piece | 2.96 mg/piece | 1.4% | 10 |
| Green Tea Extract (contains 45.7% EGCG) | EGCG: 7.54 mg/piece | EGCG content: 7.57 mg/piece | 7.5% | 6 |

*Vitamin E was supplied by Cognis Company, trade name Covitol 700WD, containing 51.5% tocopherol acetate.

Example 3

Example 3 demonstrates antioxidant release from chewing gum after 20 minutes of chewing.

| | Release of antioxidants after 20 minute chew. | | | |
|---|---|---|---|---|
| Active Compound | Active remained in gum cud | Standard Deviation | % Released | N |
| Vitamin E[3] (Tocopherol Acetate)* | 17.22 mg/piece | 31.0 mg/piece | 46% | 4 |
| Vitamin C | 1.90 mg/piece | 1.90 mg/piece | 98% | 4 |
| Gallic Acid | 0.26 mg/piece | 0.15 mg/piece | 92% | 4 |
| Green Tea Extract (contains 45.7% EGCG) | EGCG: 3.18 mg/piece | EGCG content: 0.45 mg/piece | 58% | 5 |

Vitamin E was supplied by Cognis Company, trade name Covitol 700WD, containing 51.5% tocopherol acetate.

Example 4

The chewing gum formulations of Examples 1-3 wherein the chewing gums are coated, and at least one of the antioxidant ingredients is applied to the coating.

II. Data

Clinical Design

The study was a double blind, parallel study including 21 heavy smokers, having ages between 23-65. Subjects were screened from their medical history, smoking history and serum vitamin C & E levels. Subjects met inclusion/exclusion criteria and signed informed consent, and were assigned for either the antioxidant (AO) gum group or for the placebo gum group. Each subject was instructed to chew 4 dosages of gum between meals per day, and continued for 8 weeks.

Skin biopsies were taken and apoptosis cells were analyzed at 0 (baseline) and at 8 weeks after each subject received UV exposure at the buttocks.

At 0, 4 and 8 weeks, blood was withdrawn from subjects and sent for vitamin C & E analysis. The skin biopsy was taken and apoptosis cell In addition, visual appearance assessment and digital photography was taken at 0 and 8 weeks. Subjects were required to fill out a "Chewing Diary" for daily chewing records.

Both antioxidant (AO) gum and placebo gum were made with grapefruit flavor. The AO gum contained 31.0 mg of vitamin E, 89.1 mg of vitamin C, 3.0 mg of gallic acid, and 7.57 mg of EGCG per piece. This provided daily doses to the recipients of approximately 700 mg vitamin C, 110 mg. of vitamin E, 35 mg of EGCG and 22 mg of gallic acid. The vitamin E was mixed with maltitol and dry-charged with the coating of the chewing gum, while the other antioxidants were added to the center of the chewing gum.

Results

Out of the twenty-one subjects enrolled in the study, twenty successfully completed the study. All subjects were observed to be compliant with the study procedures based on their completion of the study diaries. Two subjects demonstrated vitamin C levels higher than what could be expected from the gum supplement provided. It was believed that the two subjects did not follow the prescribed diet, and their data was excluded from the analysis.

Table 3 presents a summary of the sunburn cell count change categories at the 8 week measurement time point. For the AO gum, the changes demonstrated a decrease, while the placebo gum either increased or remained the same. The AO gum differed significantly compared with the placebo gum with respect to the distribution of change categories (chi-squared p-value=0.0104).

TABLE 3

Summary of Categorical Sunburn Cell Change Scores

| Change Category | Active | Placebo |
|---|---|---|
| −1 | 6 (85.7%) | 1 (11.1%) |
| 0 | 0 (0.0%) | 3 (33.3%) |
| 1 | 1 (14.3%) | 5 (55.6%) |

1 = Decrease;
0 = No Change;
+1 = Increase

Table 4 presents the sunburn cell counts obtained at each measurement time point, and the between treatment p-values comparing the AO and control gums. No statistically significant difference was indicated between the gums at baseline. At the 8 week time point, the mean sunburn cell count associated with the AO gum was statistically significantly lower than that associated with the control gum measured by one side p (0.0302), or marginally significantly lower than that associated with the control gum, measure by two-sided p-value (0.0604).

TABLE 4

Summary of Categorical Sunburn Cell Change Scores

| | Treatment | | | | | |
|---|---|---|---|---|---|---|
| | Active | | | Placebo | | Between-Trt. |
| | n | Mean | S.D. | n | Mean | S.D. | p-value |
| Baseline | 7 | 29.14 | 32.79 | 9 | 17.44 | 16.53 | 0.3658 |
| 8-Week | 7 | 12.71 | 10.90 | 9 | 31.22 | 27.06 | 0.0604 |

1 = Decrease;
0 = No Change;
+1 = Increase

Table 5 shows the changes between the baseline scores and the follow-up scores for each post-baseline measurement time point. For the Active gum, statistically significant increases in Vitamin C scores were indicated. For the Placebo gum, no significant difference was indicated between the scores at baseline and either of the follow-up measurements.

TABLE 5

Summary of Vitamin C Changes from Baseline

| | Treatment | | | | | | |
|---|---|---|---|---|---|---|---|
| | Active | | | | Placebo | | | |
| | n | Mean | S.D. | Within-Trt. p-value | n | Mean | S.D. | Within-Trt. p-value |
| Baseline 4 Weeks | 8 | 1.04 | 0.31 | <0.0001 | 10 | 0.24 | 0.55 | 0.2100 |
| Baseline 8 Weeks | 8 | 0.86 | 0.44 | 0.0009 | 10 | 0.12 | 0.38 | 0.3387 |

Table 6 presents the changes between the baseline scores and the follow-up scores for each post-baseline measurement time point. For the Active gum, statistically significant increases in Vitamin E scores were indicated. For the Placebo gum, no significant difference was indicated between the scores at baseline and either of the follow-up measurements

TABLE 6

Summary of Vitamin E Changes from Baseline

| | Treatment | | | | | | |
|---|---|---|---|---|---|---|---|
| | Active | | | | Placebo | | | |
| | n | Mean | S.D. | Within-Trt. p-value | n | Mean | S.D. | Within-Trt. p-value |
| Baseline 4 Weeks | 8 | 0.39 | 0.27 | 0.0051 | 10 | 0.05 | 0.13 | 0.3087 |
| Baseline 8 Weeks | 8 | 0.35 | 0.15 | 0.0003 | 10 | 0.06 | 0.19 | 0.3547 |

CONCLUSIONS

This pilot clinical study demonstrated that antioxidant gum provided significant skin protection against UV exposure compared with placebo gum with respect to the distributions of change categories after 8-week intake. At the 8-week time point, the mean sunburn cell count associated with the AO gum was statistically significantly higher than that associated with the Placebo gum with one-tail p=0.0302, or marginally statistically significant with 2-tail p=0.0604. The results also demonstrated that Antioxidant gum provided appreciable increases of blood vitamin C and E levels at both 4-week point, and at 8-week point compared with the baseline. All showed statistically significant (2-tail p<0.05). In contrast, the placebo gum provided no difference of blood vitamin C & E levels at 4-week and 8-week points.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

What is claimed is:

1. A coated chewable composition for decreasing oxidative stress caused by sunlight or ultraviolet light B (UVB) in an individual comprising:
   Vitamin C;
   Vitamin E;
   0.001% to about 20% by weight of an extract of green tea having an epigallocatechin gallate (EGCG) content of at least 20% by weight of the green tea extract; and,
   gallic acid.

2. The composition of claim 1, wherein the extract of green tea has an epigallocatechin gallate (EGCG) content of at least 40% by weight of the green tea extract.

3. The oral composition of claim 1, wherein said oral composition is selected from the group consisting of chewing gums and chewy candies.

4. The composition of claim 1, wherein the coated chewable composition comprises:
   a) 0.01% to about 10% by weight vitamin C;
   b) 0.01% to about 5% by weight vitamin E;
   c) 0.01% to about 10% by weight extract of green tea with a minimum epigallocatechin gallate (EGCG) content of 30% by weight of the green tea extract; and,
   d) 0.001% to about 2% by weight gallic acid.

* * * * *